US012133967B2

(12) United States Patent
Ding

(10) Patent No.: US 12,133,967 B2
(45) Date of Patent: *Nov. 5, 2024

(54) TEMPERATURE COMPENSATION FLOW-LIMITING DEVICE AND ELASTOMERIC INFUSION SYSTEM

(71) Applicant: HELIOS BIOMATERIALS LLC., Austin, TX (US)

(72) Inventor: Yuan-Chieh Ding, Taichung (TW)

(73) Assignee: HELIOS BIOMATERIALS LLC., Austin, TX (US)

(*) Notice: Subject to any disclaimer, the term of this patent is extended or adjusted under 35 U.S.C. 154(b) by 218 days.

This patent is subject to a terminal disclaimer.

(21) Appl. No.: 17/583,416

(22) Filed: Jan. 25, 2022

(65) Prior Publication Data

US 2022/0143309 A1    May 12, 2022

Related U.S. Application Data

(63) Continuation of application No. 16/721,138, filed on Dec. 19, 2019, now Pat. No. 11,529,462.

(30) Foreign Application Priority Data

Sep. 24, 2019  (TW) .................. 108134448

(51) Int. Cl.
*A61M 5/168*  (2006.01)
*A61M 5/148*  (2006.01)
*A61M 5/152*  (2006.01)

(52) U.S. Cl.
CPC ........ *A61M 5/16804* (2013.01); *A61M 5/148* (2013.01); *A61M 5/152* (2013.01); *A61M 2205/0216* (2013.01); *A61M 2205/3331* (2013.01); *A61M 2205/3372* (2013.01)

(58) Field of Classification Search
CPC .. A61M 5/16804; A61M 5/148; A61M 5/152; A61M 2205/3372; A61M 5/16813
See application file for complete search history.

(56) References Cited

U.S. PATENT DOCUMENTS

| 4,318,400 | A  |   | 3/1982 | Peery et al. |
| 4,769,008 | A  |   | 9/1988 | Hessel |
| 4,904,239 | A  |   | 2/1990 | Winchell et al. |
| 6,273,117 | B1 |   | 8/2001 | McPhee |
| 6,361,528 | B1 | * | 3/2002 | Wilson ............ A61M 25/0023 604/500 |
| 6,619,308 | B2 |   | 9/2003 | Massengale et al. |
| 7,341,572 | B2 |   | 3/2008 | Bridle et al. |

(Continued)

*Primary Examiner* — Bradley J Osinski
(74) *Attorney, Agent, or Firm* — Demian K. Jackson; Jackson IPG PLLC

(57) ABSTRACT

A temperature compensation flow-limiting device are provided. The temperature compensation flow-limiting device is disposed in the infusion tube of the elastomeric infusion system to improve instability, caused by changes to temperature, of the flow velocity of the fluid inside the infusion tube to keep the flow velocity of the fluid stable. The temperature compensation flow-limiting device includes an inner layer and an outer layer; the coefficient of thermal expansion (CTE) of the inner layer is greater than that of the outer layer. When the temperature of the fluid inside the infusion tube increases, the inner layer expands and the internal diameter decreases as it is limited by the outer layer.

13 Claims, 12 Drawing Sheets

(56) References Cited

U.S. PATENT DOCUMENTS

| | | |
|---|---|---|
| 7,892,213 B2 | 2/2011 | Walborn |
| 2011/0098673 A1 | 4/2011 | Walborn |
| 2011/0106048 A1 | 5/2011 | Walborn |
| 2018/0229002 A1* | 8/2018 | Charest ............ A61M 25/0029 |

* cited by examiner

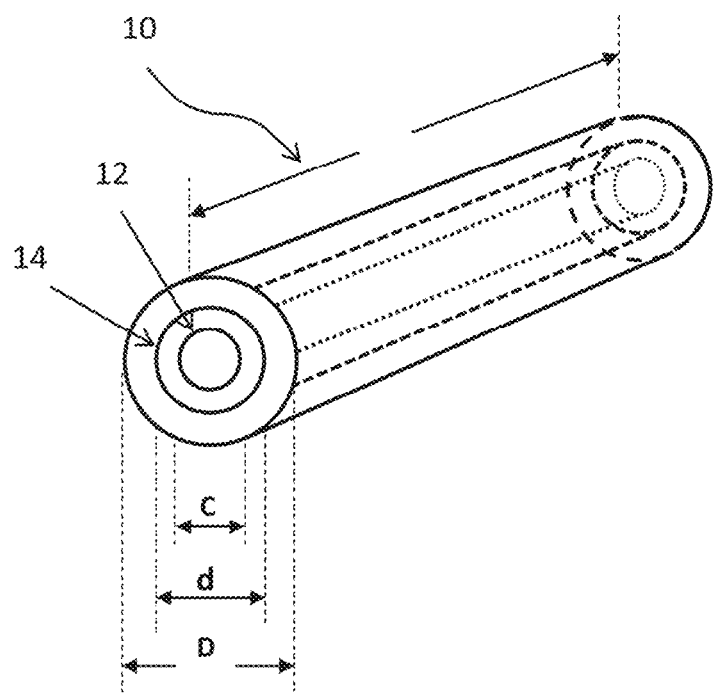
Fig. 2
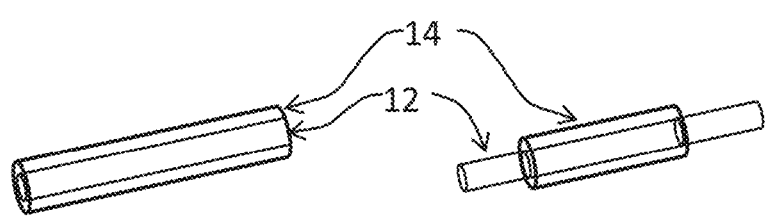
Fig. 3A                                   Fig. 3B

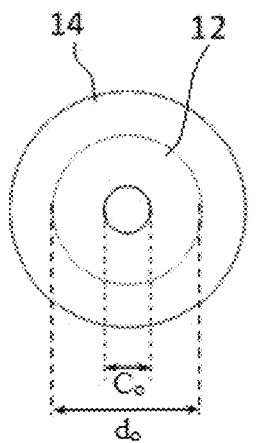
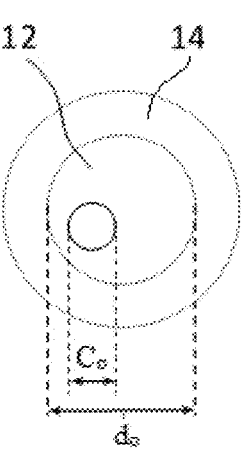
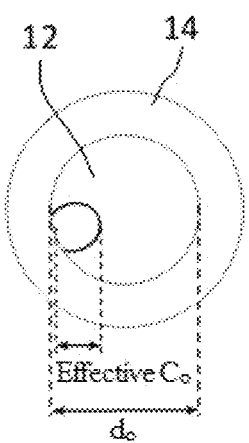
Fig. 4A          Fig. 4B          Fig. 4C
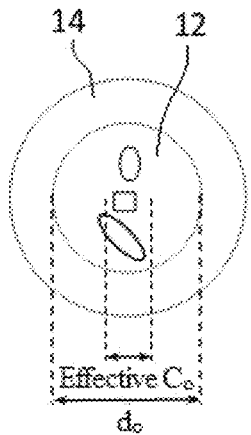
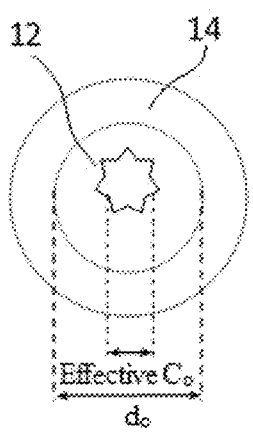
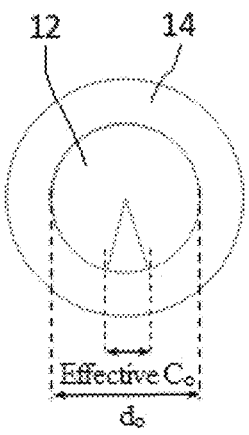
Fig. 4D          Fig. 4E          Fig. 4F
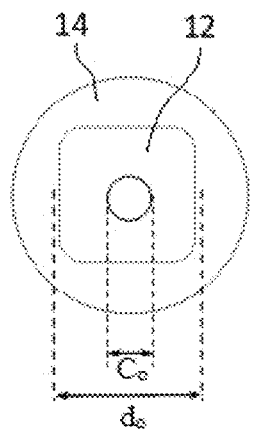
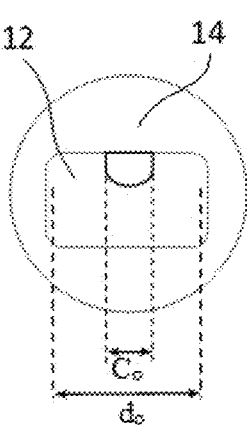
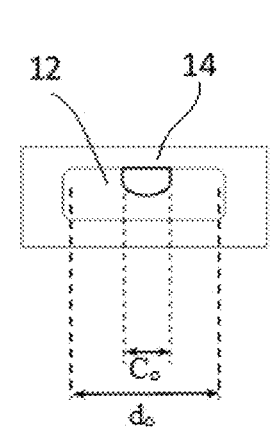
Fig. 4G          Fig. 4H          Fig. 4I

TEMPERATURE COMPENSATION FLOW-LIMITING DEVICE AND ELASTOMERIC INFUSION SYSTEM

This is a continuation application of Ser. No. 16/721,138 filed on Dec. 19, 2019.

BACKGROUND OF INVENTION

1. Field of the Invention

The present invention generally relates to an infusion system, in particular to a temperature compensation flow-limiting device with temperature compensation and flow velocity stabilizing abilities.

2. Description of the Related Art

A currently available elastomeric infusion system (EIS) (also called elastomeric infusion pump, infusion apparatus) can apply pressure to output medicinal solutions, so patients can inject medicinal solutions for themselves at home. The elastomeric infusion system does not need electricity, is of low cost, is easy to dispose of and is transportable, so is very convenient to use. However, the elastomeric infusion system should be stable and precisely operated to make patients feel comfortable and to enhance safety. Please refer to FIG. 1, which is a schematic view of the currently available elastomeric infusion system. The currently available elastomeric infusion system mainly includes housing 1 for a patient to comfortably wear the system, an infusion tube connected to one end of housing 1, support element 3 disposed inside the housing, bladder-type dispenser 4 made of rubber and capable of expanding or shrinking and disposed on support element 3 and inside housing 1 so as to generate pressure to output the medicinal solution from infusion tube 2; infusion tube 2 is further provided with tubular capillary element 5 (or restrictor, flow regulator), usually made of glass or plastic; pressure regulator 6 disposed on infusion tube 2 to regulate the flow status of the fluid output from bladder-type dispenser 4 so as to obtain stable and precise flow velocity of the medicinal solution. There are already many relevant patent literatures disclosed, such as U.S. Pat. Nos. 7,892,213B2, 7,341,572, 6,619,308, 6,273,117, 4,769,008, 4,904,239, 4,318,400, US publication No. 20110106048A1 and US publication No. 20110098673 A1.

The flow velocity of the medicine solution of an ideal elastomeric infusion system should be consistent and precise. It is not acceptable if the flow rate is too high or too low (currently, it is considered acceptable if the flow rate of the elastomeric infusion system is within the range of the standard flow rate±10%). However, when the bladder-type dispenser is emptying, the pressure and flow velocity thereupon significantly changes; thus, the flow rate of the medicinal solution is not stable. As shown in FIG. 1, the currently available elastomeric infusion system is further provided with a pressure regulator to overcome pressure change, such that the flow status of the fluid output from the bladder-type dispenser can be adjusted to make the flow velocity of the medicinal solution stable and precise.

In addition, the analysis shows that the factors resulting in the change of pressure and flow velocity of the medicinal solution further include influences caused by the temperature of the medicinal solution changing. The environmental temperature change of the elastomeric infusion system in a house is usually 5-40° C. As the heat expansion effect occurs when the temperature increases, the diameters of the infusion tube and the capillary element will increase; in the meantime, the viscosity of the medicinal solution decreases. The combination of the above two factors will increase the flow velocity and the flow rate of the medicinal solution in the infusion tube and the capillary element; a decrease in temperature will result in a contrary result. Obviously, how to overcomes the influences of the change of the flow velocity due to temperature change becomes an emergent issue in terms of the operation safety of EIS. Several patent literatures, such as U.S. Pat. No. 7,892,213B2, U.S. Pat. No. 4,904,239, US publication No. 20110106048A1 and US publication No. 20110098673A1, disclose that the capillary element is fixed on the skin of the patient and keeps the temperature of the medicinal solution relatively consistent via the body temperature of the patient. However, the above method is to reduce influence to the viscosity of the medicinal solution by reducing the change of the environment temperature via the way of using the device. The inventor of the present invention considers that it is necessary to change the design of the capillary element to completely solve the above problem.

SUMMARY OF THE INVENTION

Therefore, it is the primary objective of the present invention to provide a temperature compensation flow-limiting device, which can improve the instability of the flow rate caused by changes to temperature, and provide a consistent and stable flow rate curve for patients to ensure safe use of the device.

To achieve the foregoing objective, the present invention provides a temperature compensation flow-limiting device disposed in the infusion tube of an infusion system, and including an inner layer and an outer layer. The coefficient of thermal expansion of the inner layer is greater than the coefficient of thermal expansion of the outer layer. When the temperature of the fluid inside the infusion tube increases, the inner layer expands and the internal diameter of the inner layer decreases as it is limited by the outer layer.

BRIEF DESCRIPTION OF THE DRAWINGS

The detailed structure, operating principle and effects of the present invention will now be described in more detail hereinafter, with reference to the accompanying drawings that show various embodiments of the invention as follows.

FIG. 2 is a perspective view of the temperature compensation flow-limiting device in accordance with the present invention.

FIG. 3(a) and FIG. 3(b) are schematic views of the inner layer aligned with the outer layer and the inner layer not aligned with the outer layer of the temperature compensation flow-limiting device in accordance with the present invention.

FIG. 4(a), FIG. 4(b), FIG. 4(c), FIG. 4(d), FIG. 4(e), FIG. 4(f), FIG. 4(g), FIG. 4(h) and FIG. 4(i) are schematic views of different cross-sections of the temperature compensation flow-limiting device in accordance with the present invention.

DETAILED DESCRIPTION OF THE PREFERRED EMBODIMENTS

Figure 1:
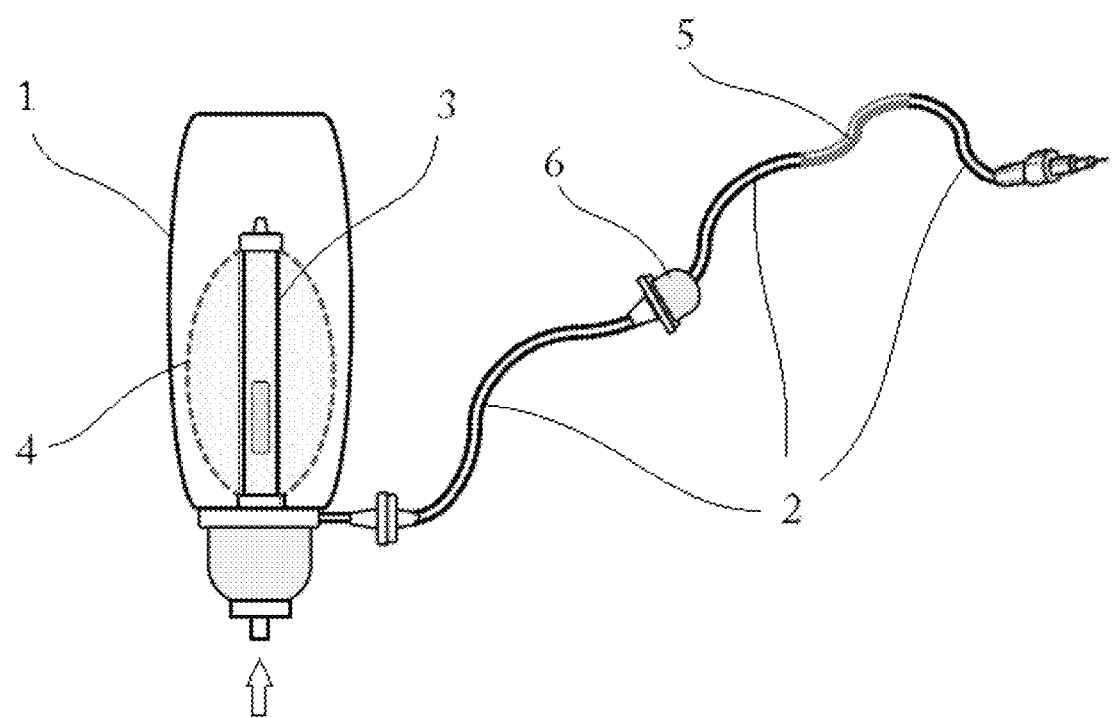
FIG. 1 is a structure diagram of the currently available elastomeric infusion system.

The technical content of the present invention will become apparent by the detailed description of the embodiments and the illustration of related drawings as follows.

Please refer to FIG. 2 and FIG. 3. Temperature compensation flow-limiting device 1 in accordance with the preferred embodiment of the present invention is disposed in an elastomeric infusion system. The elastomeric infusion system includes housing, an infusion tube connected to one end of the housing for output of medicinal solution, a support element disposed inside the housing, a bladder-type dispenser made of elastic material and capable of expanding or shrinking, and disposed on the outer side of the support element and inside the housing so as to generate elastic shrinking pressure to output the medicinal solution from the infusion tube, a pressure regulator to adjust the flow status of the fluid output from the bladder-type dispenser to obtain stable and precise flow velocity of the medicinal solution (optional). Temperature compensation flow-limiting device 10 is connected to the infusion tube. The housing, the infusion tube, the support element and the bladder-type dispenser are similar to the elements of the currently available infusion apparatus, so the detailed structures and the operational methods of the housing, the infusion tube, the support element and the bladder-type dispenser will not be described therein. Temperature compensation flow-limiting device 10 includes inner layer 12 and an outer layer 14. The two ends of inner layer 12 can be aligned with the two ends of outer layer 14, as shown in FIG. 3(a), or the two ends of inner layer 12 can protrude from the two ends of outer layer 14, as shown in FIG. 3(b). Inner layer 12 is stably adhered to outer layer 14, and can be manufactured by co-extrusion or injection molding to avoid inner layer 12 being separated from outer layer 14 when in use. Furthermore, the coefficient of thermal expansion (CTE) of inner layer 12 is greater than that of outer layer 14.

Accordingly, when the temperature of the fluid inside the infusion tube increases, inner layer 12 may expand but the internal diameter thereof decreases as it is limited by outer layer 14. Through a combination of the diameter change of inner layer 12 and a change of the viscosity of the fluid, the flow velocity of the fluid transported by inner layer 12 can be stabilized. More specifically, when the temperature increases, the viscosity of the fluid decreases, so the flow velocity of the fluid increases. However, the diameter of the inner layer 12 shrinks, resulting in a decrease of flow velocity. The above two processes can compensate for each other and result in a stable flow rate, and vice versa.

Besides, outer layer 14 of temperature compensation flow-limiting device 10 surrounds and seals inner layer 12, and the shape of outer layer 14 is not limited. The shape and the quantity of the inner channel of inner layer 12 are also not limited, which can even be eccentric. For the inner channel with different cross-sections, quantities and eccentric positions of inner layer 12, $C_o$ can be considered the diameter of the circular inner channel with the equivalent cross-section area. Similarly, for outer layer 14 with different shapes, $d_o$ can be considered the diameter of circular outer layer 14 with the equivalent cross-section area. Meanwhile, the circular diameters calculated according to the equivalent cross-section area can be called the effective diameter. For the structure of the inner layer and the outer layer with different cross-section shapes, inner channel quantities and eccentric positions, when a structure conforms to the aforementioned structure with the outer layer hard and the inner layer soft, the structure should be considered consistent with the temperature compensation flow-limiting device of the present invention. Examples are as shown in FIG. 4(a): concentric circle channel structure, that is, the inner layer 12 and the inner channel of the inner layer 12 are on the same axis; FIG. 4(b): eccentric circle channel structure, that is, the inner channel and the inner channel of the inner layer have different axis; FIG. 4(c): hole-type channel contacting the outer layer, that is, the inner channel of the inner layer 12 is partially connected to the outer layer 14; FIG. 4(d): multi-channel structure, that is, multiple inner channels inside the inner layer 12; FIG. 4(e): polygon channel structure, that is, the cross section of the inner channel of the inner layer 12 is polygonal; FIG. 4(f): triangle channel contacting the outer layer, that is, the inner channel of the inner layer 12 is partially connected to the outer layer 14 and the cross section of the inner channel of the inner layer 12 is triangular; FIG. 4(g): non-circle inner layer structure, that is, the cross section of the inner channel of the inner layer 12 is non-circle; FIG. 4(h): rectangular inner groove channel, that is, the cross section of the inner layer 12 is rectangular and the inner channel of the inner layer 12 is partially connected to the outer layer 14; FIG. 4(i): flat-type groove structure, that is, the cross section of the inner layer 12 and the outer layer 14 are flat rectangular type, and the inner channel of the inner layer 12 is partially connected to the outer layer 14. $d_o$ shown in the drawings stands for the external diameter of the inner layer 12 and $C_o$ stands for the diameter of the inner channel of the inner layer 12, which is the diameter of the channel for transporting the fluid.

In addition, temperature compensation flow-limiting device 10 is not limited to at least two layers of tube-type structures; temperature compensation flow-limiting device 10 can also have at least two layers of flat structures. The manufacturing method thereof can not only be conventional techniques such as extrusion, injection, grouting and sealing, etc., but can also be a layer-shaped groove-type structure formed by the MEMS method, as shown in FIG. 4(i).

Figure 5:
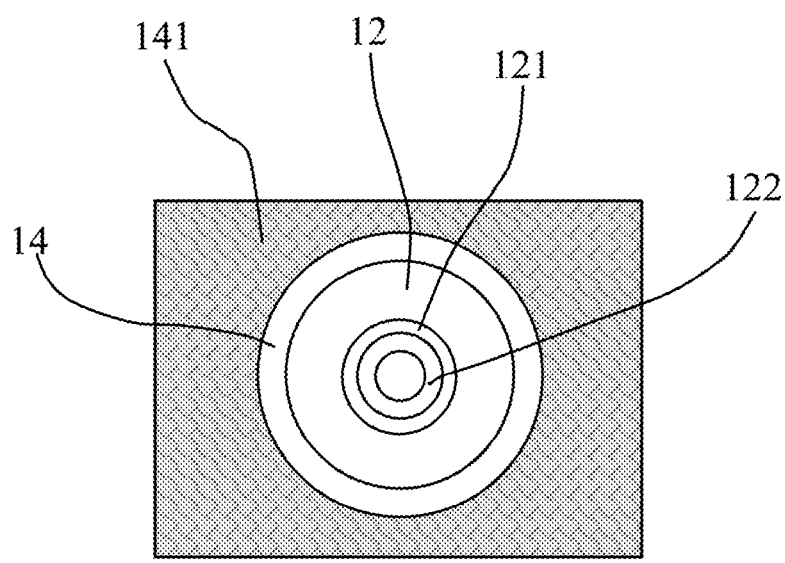
FIG. 5 is a schematic view of the inner layer and the outer layer further provided with supplementary layers of the temperature compensation flow-limiting device in accordance with the present invention.

Moreover, temperature compensation flow-limiting device 10 is not limited to a double-layer structure consisting of inner layer 12 and outer layer 14. As shown in FIG. 5, the inner side of inner layer 12 and the outer side of outer layer 14 can be further provided with several supplementary layers 121, 122, 141 so as to generate additional medical-care functions, such as supplementary layers made of low protein absorption material, with anti-reaction function for medicines or other various purposes. However, the supplementary layers do not influence the performances of inner layer 12 and outer layer 14.

Furthermore, inner layer 12 and outer layer 14 can be made of the same material or different materials, and the materials may be one of polymer, ceramic, glass and metal. When inner layer 12 and outer layer 14 are made of different materials, inner layer 12 may be one of several flexible plastic materials, including PVC or thermoplastic polyurethanes (TPU); outer layer 12 may be a flexible plastic material, including ABS, MABS, reinforced urethane elastomer, etc. The CTE of inner layer 12 is 130-200 ppm/° C. and the CTE of outer layer 14 is lower than 110 ppm/° C., as shown in Table 1.

TABLE 1

| Type of polymers for inner layer | Inner layer | Outer layer |
| --- | --- | --- |
| Flexible PVC | Flexible PVC, softer grade, e.g. 40A shore hardness PVC such as Colorite 4011G-015 grade, and up to 95A hardness PVC such as Colorite 9511G-015 grade, where the CTE is about 150-200 ppm/C | ABS such as IneosLustran 2710 with CTE = 90 ppm/C; MABS such as Terlux 2802 with CTE = 80-110 ppm/C; Reinforced urethane elastomer such as Bayflex 110-50 with CTE~76 ppm/C Glass and ceramics Metallic materials |
| Thermoplastic polyurethane (TPU) | Softer grade TPU, e.g. Pellethane 2363-80A, CTE = 177 ppm/C; 2363-90AE, CTE = 162 ppm/C; 2363-90A, CTE = 157 ppm/C; | ABS such as IneosLustran 2710 with CTE = 90 ppm/C; MABS such as Terlux 2802 with CTE = 80-110 ppm/C; Reinforced urethane elastomer such as Bayflex 110-50 with CTE~76 ppm/C Glass and ceramic Metallic materials |
| Thermoplastic polyamide | Softer grade of Pebax, such as 2533 SA, CTE~200 ppm/C 3533 SA, CTE~200 ppm/C | ABS such as IneosLustran 2710 with CTE = 90 ppm/C; MABS such as Terlux 2802 with CTE = 80-110 ppm/C; Reinforced urethane elastomer such as Bayflex 110-50 with CTE~76 ppm/C Glass and ceramic Metallic materials |
| Thermoplastic polyester | Softer grade of Hytrel, such as 4056, CTE = 130-160 ppm/C 5556, CTE = 160-180 ppm/C | ABS such as IneosLustran 2710 with CTE = 90 ppm/C; MABS such as Terlux 2802 with CTE = 80-110 ppm/C; Reinforced urethane elastomer such as Bayflex 110-50 with CTE~76 ppm/C Glass and ceramic Metallic materials |

When inner layer 12 and outer layer 14 are made of the same material, the material of inner layer 12 and the material of outer layer 14 may be the same but have different formulas, molecular weights and/or filling materials, which may be one of several flexible plastic materials, including PVC or polyolefin polymer, as shown in Table 2.

TABLE 2

| Type of polymers | Inner layer | Outer layer |
|---|---|---|
| Flexible PVC | flexible PVC, softer grade, e.g. 40A hardness, such as Colorite 4011G-015 grade | Flexible PVC, more rigid grade, e.g. 95A hardness, such as Colorite 9511G-015 grade |
| Thermoplastic polyurethane (TPU) | Softer grade TPU, e.g. Pellethane 2363-80A, CTE = 177 pp/C; 2363-90AE, CTE = 162 ppm/C; 2363-90A, CTE = 157 ppm/C; | More rigid grade TPU, e.g. Pellethane 2363-55D, CTE = 143 ppm/C; 2363-65D, CTE = 104 ppm/C; 2363-75D, CTE = 89 ppm/C |
| Thermoplastic polyamide | Softer grade of Pebax, such as 2533 SA, CTE~200 ppm/C 3533 SA, CTE~200 ppm/C | More rigid grade of Pebax, such as 5533 SA, CTE~170 ppm/C 6333 SA, CTE~140 ppm/C |
| Thermoplastic polyester | Softer grade of Hytrel, such as 4056, CTE = 130-160 ppm/C 5556, CTE = 160-180 ppm/C | More rigid grade of Hytrel, such as 8238, CTE = 100-140 ppm/C |
| Polyolefin polymer | Various soft polyolefin, such as EVA, ULDPE | LDPE, MDPE, HDPE, PP, ionomer |

In addition, outer layer 14 can be further provided with materials with negative thermal expansion (NTE) and/or low coefficient of thermal expansion (CTE), which may be polymer, ceramic, glass, alloy, etc. Materials with negative thermal expansion (NTE) may be one of β-eucryptite or $ZrW_2O_8$ material, as shown in Table 3.

TABLE 3

| Materials | ΔV/V [%] | $T_{NTE}$ [K] | ΔT [K] | CTE [ppm/K][a] | Structure[b] | Category[c] | Method[d] |
|---|---|---|---|---|---|---|---|
| β-eucryptite | 0.15 | 293-1073 | 780 | −0.6 | Hexagonal | CV | X |
| $ZrW_2O_8$ | 2.7 | 2-1443 | 1441 | −6 to −9 | Cubic | CV | D/N |
| $Cd(CN)_2 \cdot xCCl_4$ | 2.1 | 170-375 | 205 | −34 | Cubic | CV | X |
| $Mn_3Ga_{0.7}Ge_{0.3}N_{0.88}C_{0.12}$ | 0.5 | 197-319 | 122 | −18 | Cubic | MG | D |
| $LaFe_{10.5}Co_{1.0}Si_{1.5}$ | 1.1 | 240-350 | 110 | −26 | Cubic | MG | D |
| $MnCo_{0.98}Cr_{0.02}Ge$ | 3.2 | 122-332 | 210 | −52 | Orthorhombic | MG | D |
| $0.4PbTiO_3$—$0.6BiFeO_3$ | 2.7 | 298-923 | 625 | −13 | Tetragonal | FE | X |
| $SrCu_3Fe_4O_{12}$ | 0.4 | 180-250 | 70 | −20 | Cubic | CT | X |
| $Bi_{0.95}La_{0.05}NiO_3$ | 2 | 320-380 | 60 | −82 | Triclinic | CT | D |
| $Sm_{2.75}C_{60}$ | 0.8 | 4-30 | 26 | −100 | Orthorhombic | CT | X |
| $Ca_2Ru0.9Mn_{0.1}O_4$ | 0.8 | 150-400 | 250 | −10 | Orthorhombic | MI | X |
| AgI | 6 | 430 | — | — | Hexagonal | Others | X |

Microstructural effects are not considered. Parameters of materials with phase transition accompanied by large volume contraction upon cooling, not broadened, are also listed for comparison.
[a]Averaged value when the material is anisotropic.
[b]NTEregion or lower-temperature, larger-volume phase.
[c]CV, conventional; MG, magnetic transition; FE, ferroelectric transition; CT, charge-transfer transition; MI, metal-insulator transition.
[d]D, dilatometry; N, neutron diffraction; X, X-ray diffraction.

Materials with low coefficient of thermal expansion (CTE) may be one of $SiO_2$—$Al_2O_3$—$Li_2O$ or $Ca_{0.5}Zr_2P_3O_{12}$, as shown in Table 4.

TABLE 4

| Substance | Crystalline phase | CTE(ppm/K) |
|---|---|---|
| $SiO_2$—$Al_2O_3$—$Li_2O$ | β-spodumene, β-eucryptite, β-quartz | −5~34 |
| $SiO_2$—$Al_2O_3$—MgO | Magnesium pyrophosphate Cordierite | 0~15 |
| $SiO_2$—$Al_2O_3$—ZnO | β-quartz, gahnite | −5~31 |
| $3Al_2O_3 \cdot 2SiO_2$ | Mullite | 4.5 |
| $Si_3N_4$ | | 3.0 |
| Si | | 4 |
| $B_4C$ | | 4.5 |
| $TiB_2$ | | 4.5 |
| $Ca_{0.5}Zr_2P_3O_{12}$ | $\alpha$-$Zn_3(PO_4)_2$, $Mg_3(PO_4)_2$ | −1~1 |

As described above, inner layer 12 and outer layer 14 may be made of the same material. Although temperature compensation flow-limiting device 10 is a double-layer structure according to the viewpoint of thermal expansion, the two layers are made of a continuous substrate of the same material (the primary phase; the secondary phase is a material with low/negative CTE). Therefore, the interface between the two layers disappears; in other words, the interface between the two layers will not be formed, just like a composite material. A material with low/negative CTE is not limited to the form of particles, whiskers, fibers, microspheres, slices, rings, etc.

The following simulation uses the stability coefficient S to estimate temperature compensation flow-limiting device 10 (capillary tube) adopting a single-layer structure or double-layer structure; the flow rate stabilization effect in different temperatures can be better.

The capillary discussed here may be considered as a micro-scale mass transfer system, in which the pressure drop, ΔP, may affect the flow, Q, is given by a Hagen-Poiseuille type formula [3]:

$$\Delta P = \frac{8\mu L Q}{\pi R^4} \quad (1)$$

and can be rearranged as $$Q = \frac{\Delta P \cdot \pi R^4}{8\mu L} \quad (2)$$

where ΔP is the pressure gap between the proximal and distal ends and is considered as a constant when using a pressure regulator, μ is the viscosity of the fluid, Q the volumetric flow rate of the fluid and R the radius of the conduit.

In Eq. (2), ΔP is can be a constant if there is a pressure regulator installed between the elastic bladder and the flow restrictor. Thus, Q is determined by R, L and μ, which are all functions of temperature; and Eq. (2) may be reformed as $$Q(T) = k \cdot \frac{R(T)^4}{\mu(T) \cdot L(T)} \quad (3)$$

By simple dimension analysis, Q(T) is proportional to viscosity μ(T) and third order of length R(T)³. Now, if the temperature range is restricted between 5 to 45° C., the maximum temperature gap ΔT is 40° C. The thermal expansion coefficient of most capillary is among 30-150 ppm/° C., and it is multiplied by ΔT, 40° C., the variation of radius (length dimension) is in a range of 10⁻³ order. The drug fluid is mostly water, of which the viscosity is 1 cp at 20° C. When temperature changes to 5° C. and 45° C., its viscosity approaches to 1.52 cp and 0.59 cp, respectively. If we look at the variation between radius and viscosity at temperatures of 5 to 45° C., it is obvious that viscosity is the dominant factor to cause the flow rate change.

A mathematical model has been proposed here to understand the flow volume related to the single/double-layered structure of the capillary. As shown in FIG. 2, a schematic diagram of the double-layered capillary was drawn, in which the capillary consists of an outside layer with thermal expansion coefficient of E and thickness of T and an inner layer with the thermal expansion coefficient of e and the thickness of t. Assume that the length of the capillary is L, the outside diameter of the capillary is D, the diameter of the inner layer is d, and the diameter of the core (hollow conduit) is C. Noted that when E equals to e, it becomes a single-layered structure.

For a single layer capillary, where D=d and E=e, therefore we only consider the inner layer for the single-layered structure. According to the definition of thermal expansion, the following equation is always valid, $$d(T) = d_o \cdot (1 + e\Delta T) \quad (4)$$

The length of the capillary L(T) at temperature T is determined by $$L(T) = L_o \cdot (1 + e\Delta T) \quad (5)$$

C(T) may be obtained as Eq. (6):

$$C(T) = c_o[1 + e(\Delta T)] \quad (6)$$

Now we recall the Hagen-Poiseuille equation, i.e., Eq. (2):

$$Q = \frac{\Delta P \cdot \pi R^4}{8\mu L} \quad (2)$$

When temperature moves away from its initial state, the new volumetric flow rate transforms to Eq. (7) because flow rate Q is a function of temperature:

$$Q(T) = \frac{\Delta P \cdot \pi \cdot R(T)^4}{8\mu(T) \cdot L(T)} = \frac{\Delta P \cdot \pi \cdot C(T)^4}{128\mu(T) \cdot L(T)} \quad (7)$$

Where R=0.5 C and ΔP is considered as a constant in our case.

To observe the deviation of volumetric flow rate due to temperature variation, the ratio of Q(T)/Q$_o$ may be used as a stability factor:

$$S = \frac{Q(T)}{Q_0} = \left(\frac{C(T)}{C_o}\right)^4 \cdot \left(\frac{1}{1+e\Delta T}\right) \cdot \left(\frac{\mu_0}{\mu(T)}\right) \quad (8)$$

If the content of the fluid is mainly water, we may use the viscosity of water as a function of temperature for the calculation. For water, it follows the relationship described below in a temperature range of 5 to 45° C.

$$\mu(T) = 1.022 \cdot \mu_o \cdot e^{-0.024 \cdot \Delta T} \quad (9)$$

Combine Eqs. (8) & (9), the stability factor S is redefined as the following equation, $$S = \frac{Q(T)}{Q_0} = \left(\frac{C(T)}{C_o}\right)^4 \cdot \left(\frac{1}{1+e \cdot \Delta T}\right) \cdot \left(\frac{1}{1.022 e^{-0.024 \cdot \Delta T}}\right) \quad (10)$$

And Eq. (10) may simplified to Eq. (11):

$$S = \frac{Q(T)}{Q_o} = (1 + e \cdot \Delta T)^3 \cdot \left(\frac{1}{1.022 e^{-0.024 \cdot \Delta T}}\right) \quad (11)$$

Here, when Q(T) equals to $Q_0$ (i.e., S=1), it becomes the ideal condition for a capillary of stable volumetric flow. When deviation takes place between Q(T) and $Q_0$, it is acceptable for an elastomeric infusion system if the ratio $Q(T)/Q_0$ is within ±10% (i.e., 1.1≥S≥0.9). By Eq. (14), we may find that if the value of e is negative, it is possible to control S in a range of 1.1 to 0.9. Simulated results will be provided and discussed later.

A double-layered micro-tube has been selected to form the capillary, in which the coefficient of thermal expansion (CTE) of the inner layer is larger than that of the outer layer. This double-layered capillary has strong bonding between the two layers to prevent it from delamination during use. The low CTE layer is more rigid than the high CTE layer. The thermal expansion behavior of such a double-layered capillary is a compounded result determined by the CTE of the two layers, which implies we may keep the flow rate of the capillary immune from the variation of ambient temperatures by manipulating E and e. Since E and e vary with temperatures linearly and let's assume that the value of e is much larger than that of E, i.e. e>E, and a model may be proposed as the following:

$$D(T) = D_o \cdot (1 + E\Delta T) \quad (12)$$

Where D(T) is the diameter of the outer layer at temperature of T; $D_o$ the diameter at initial temperature; E, the thermal expansion coefficient of outer layer; and ΔT, the temperature difference between temperatures of $T_o$ and T. Since the interfacial bonding between the two layers must be strong enough without delamination during the product storage and usage condition, we may logically suppose that (i) the outer layer is more rigid that its thermal expansion is not affected by the soft inner layer; (ii) the volume expansion of the inner layer is following the constraint from the outer layer, which means D(T) and L(T) will affect the value of d(T) and d(T) follows D-layer's linear expansion; (iii) L(T) is determined by D-layer due to strong adhesion between inner and outer layers. Thus, the following relations may be created, $$d(T) = d_o[1 + E(\Delta T)] \quad (13)$$

$$L(T) = L_o[1 + E(\Delta T)] \quad (14)$$

The length of the capillary L(T) at temperature T is determined by the layer of higher rigidity. When temperature changes, the volume of the inner layer, i.e. d-layer, is a function of temperature which can be calculated by the equation as follows:

$$V_d(T) = V_d^o \cdot (1 + e\Delta T)^3 \quad (15)$$

If we take the ratio of $V_d(T)/V_d^o$, it equals to the ratio of $A_d(T) \cdot L(T)/A_o \cdot L_o$; where $V_d^o$, $V_d(T)$, $A_o$ and $A_d(T)$ are the volume and cross-sectional area of the d-layer of the capillary at $T_o$ and T. Thus, we may obtain the following equation, $$\frac{V_d(T)}{V_d^o} = [1 + e(\Delta T)]^3 = \frac{A(T)}{A_0} \cdot \left(\frac{L(T)}{L_0}\right) = \left[\frac{\pi[d^2(T) - C^2(T)]}{\pi[d_0^2 - C_0^2]}\right] \cdot \left(\frac{L(T)}{L_0}\right) \quad (16)$$

Combining Eqs. (13), (14) and (16), C(T) may be solved and shown in Eq. (17):

$$C(T) = d_o \cdot \sqrt{(1 + E \cdot \Delta T)^2 - \frac{(1 - e \cdot \Delta T)^3 \cdot \left[1 - \left(\frac{C_o}{d_0}\right)^2\right]}{(1 + E \cdot \Delta T)}} \quad (17)$$

Now we recall Hagen-Poiseuille equation Eq. (7):

$$Q(T) = \frac{\Delta P \cdot \pi \cdot R(T)^4}{8\mu(T) \cdot L(T)} = \frac{\Delta P \cdot \pi \cdot C(T)^4}{128\mu(T) \cdot L(T)} \quad (7)$$

and replace C(T) of Eq. (6) by that of Eq. (17), the stability factor S for type II capillary may be obtained as shown in Eq. (18):

$$S = \frac{Q(T)}{Q_o} = \left(\frac{C(T)}{C_o}\right)^4 \cdot \left(\frac{1}{1 + E \cdot \Delta T}\right) \cdot \left(\frac{\mu_0}{\mu(T)}\right) \quad (18)$$

By substituting Eq. (9) into Eq. (18), the stability factor S of type II capillary may be written as Eq. (19):

$$\mu(T) = 1.022 \cdot \mu_o \cdot e^{-0.024 \cdot \Delta T} \quad (9)$$

$$S = \frac{Q(T)}{Q_o} = \left(\frac{C(T)}{C_o}\right)^4 \cdot \left(\frac{1}{1 + E \cdot \Delta T}\right) \cdot \left(\frac{1}{1.022 \, e^{-0.024 \cdot \Delta T}}\right) \quad (19)$$

For a type II capillary, if the CTE of the outer layer is smaller than that of the inner layer, i.e. E<e, the deviation of volumetric flow rate due to viscosity decrease shall be compensated by the reduction of core-diameter as temperature increases, and vise verse. Because the outer rigid shell constrains the inner soft layer and push the inner layer to expand toward the core region as temperature increases. We will prove this idea in later section.

The stability factor S is used to evaluate the temperature compensation fluid-limiting device 10 (capillary). The single-layer structure or the two-layer structure is used to stabilize the flow rate at different temperatures:

According to Eq. (11), all the materials of positive thermal expansion (PTE) coefficients will behave like the curve of Ex. 1 shown in FIG. 6. In theory, it is possible to stabilize the flow rate if the thermal expansion coefficient of the capillary is negatively large enough so that the volume change of the core is capable to compensate the change of flow-volume caused by viscosity variation at various temperatures. Based upon Eq. (11), examples have been summarized in Table 5, in which a nice fit of S-factor curve within the 0.9-1.1 range can be obtained. Ex. 6 and Ex. 7 appear to be very stable in flow rate when the negative thermal expansion coefficient approaches to the range between −7000 ppm/° C. and −8000 ppm/° C. Above and below this range, the S-factor curve is quickly deviating away from the safety zone.

TABLE 5

Stability factors S, calculated from Eq. (11).

| ΔT (° C.) | Ex. 1 Single layer | Ex. 2 Single layer | Ex. 3 Single layer | Ex. 4 Single layer | Ex. 5 Single layer |
|---|---|---|---|---|---|
| −15 | 0.6587 | 0.6572 | 0.6587 | 0.659 | 0.8378 |
| −10 | 0.7658 | 0.7646 | 0.7658 | 0.766 | 0.8865 |
| −5 | 0.8791 | 0.8785 | 0.8791 | 0.8793 | 0.9467 |
| 0 | 0.9984 | 0.9948 | 0.9984 | 0.9984 | 0.9984 |
| 5 | 1.1236 | 1.1244 | 1.1236 | 1.1234 | 1.0414 |
| 10 | 1.2544 | 1.2563 | 1.2544 | 1.254 | 1.0755 |
| 15 | 1.3904 | 1.3936 | 1.3904 | 1.3898 | 1.1005 |
| 20 | 1.5321 | 1.5367 | 1.5321 | 1.5312 | 1.1169 |
| e (=E) | 0.00015 | 0.00005 | 0 | −0.00001 | −0.005 |
| μ (20 C.) (mPa · s) | 0.001 | 0.001 | 0.001 | 0.001 | 0.001 |
| C (20 C.) (mm) | 0.12 | 0.12 | 0.12 | 0.12 | 0.12 |
| d (20 C.) (mm) | 1 | 1 | 1 | 1 | 1 |
| ΔP (psi) | 5 | 5 | 5 | 5 | 5 |
| L (20 C.) (cm) | 8 | 8 | 8 | 8 | 8 |

| ΔT (° C.) | Ex. 6 Single layer | Ex. 7 Single layer | Ex. 8 Single layer | Ex. 9 Single layer | Ex. 10 Single layer |
|---|---|---|---|---|---|
| −15 | 0.9178 | 0.9597 | 0.9631 | 0.6888 | 0.6616 |
| −10 | 0.9383 | 0.9646 | 0.9917 | 0.789 | 0.7681 |
| −5 | 0.9747 | 0.9889 | 1.0032 | 0.8924 | 0.8804 |
| 0 | 0.9984 | 0.9984 | 0.9984 | 0.9984 | 0.9984 |
| 5 | 1.0097 | 0.9941 | 0.9786 | 1.1068 | 1.1219 |
| 10 | 1.009 | 0.9768 | 0.9453 | 1.2171 | 1.2506 |
| 15 | 0.9968 | 0.9475 | 0.8999 | 1.3288 | 1.3842 |
| 20 | 0.9745 | 0.9081 | 0.8447 | 1.442 | 1.5229 |
| e(=E) | −0.007 | −0.008 | −0.009 | −0.001 | −0.0001 |
| μ (20 C.) (mPa · s) | 0.001 | 0.001 | 0.001 | 0.001 | 0.001 |
| C (20 C.) (mm) | 0.12 | 0.12 | 0.12 | 0.12 | 0.12 |
| d (20 C.) (mm) | 1 | 1 | 1 | 1 | 1 |
| ΔP (psi) | 5 | 5 | 5 | 5 | 5 |
| L (20 C.) (cm) | 8 | 8 | 8 | 8 | 8 |

Figure 6:
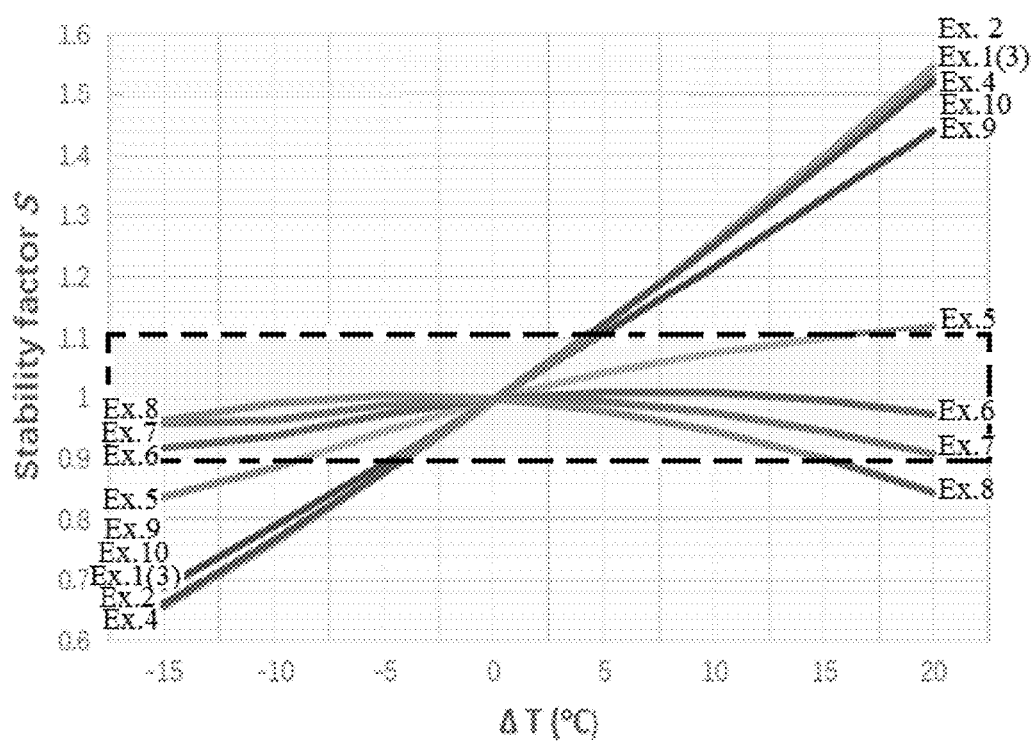
FIG. 6 is a curve chart of the stability factor S of the simulation result of several examples of the temperature compensation flow-limiting device adopting a single-layer structure in accordance with the present invention.

In Table 5, S-factor curves of Ex. 1 to Ex. 10 were drawn in FIG. 6. It proves that convergence of the S-factors within 0.9-1.1 range could be achieved as long as the CTE is negatively large enough. However, practically speaking, there is no way to find such a negative CTE material of 7000-8000 ppm/° C. That is to say, it is very difficult to solve the flow-volume stability issue by using the capillary of single-layered structure in an elastomeric infusion system.

Calculations based upon Eqs. (17) & (19) have generated a group of simulated data shown in Table 6, in which the stability factor S of the double-layered capillary is much closer to 1 than that of a single layered capillary. In Ex. 12 and Ex. 21, the stability factor S are within ±10% range in temperatures between 5° C. to 40° C. If comparing example 1 to examples 2 to 12, it is obvious that the capillaries of type II show dramatical improvement in the flow-volume stability at various temperatures. Here, the idea has been proved successfully that a double-layered core-shell structure with soft inner layer (higher CTE) and rigid outer layer (lower CTE) can achieve much better flow volume stability in the elastomeric infusion system as long as there is an appropriate combination among the parameters of E, e, $C_o$, $d_o$ and ΔP.

TABLE 6

Stability factors S, calculated from Eqs. (17) & (19).

| ΔT (° C.) | Ex. 1 Single layer | Ex. 11 Double layer | Ex. 12 Double layer | Ex. 13 Double layer | Ex. 14 Double layer | Ex. 15 Double layer |
|---|---|---|---|---|---|---|
| −15 | 0.6587 | 0.8713 | 0.9043 | 0.9428 | 0.9672 | 0.992 |
| −10 | 0.7658 | 0.9271 | 0.9515 | 0.9798 | 0.9977 | 1.0156 |
| −5 | 0.8791 | 0.9696 | 0.9829 | 0.9983 | 1.0079 | 1.0177 |
| 0 | 0.9984 | 0.9984 | 0.9984 | 0.9984 | 0.9984 | 0.9984 |
| 5 | 1.1236 | 1.0135 | 0.9982 | 0.9808 | 0.97 | 0.9593 |
| 10 | 1.2544 | 1.0149 | 0.9826 | 0.9463 | 0.924 | 0.9019 |
| 15 | 1.3904 | 1.0025 | 0.952 | 0.896 | 0.8618 | 0.8282 |
| 20 | 1.5321 | 0.9774 | 0.908 | 0.8318 | 0.7859 | 0.7412 |
| e | 0.00015 | 0.00015 | 0.00015 | 0.00015 | 0.00015 | 0.00015 |
| E | N.A. | 0.0001 | 0.000093 | 0.000085 | 0.00008 | 0.000075 |
| μ (20 C) (mPa · s) | 0.001 | 0.001 | 0.001 | 0.001 | 0.001 | 0.001 |

TABLE 6-continued

| Stability factors S, calculated from Eqs. (17)& (19). | | | | | | |
|---|---|---|---|---|---|---|
| C (20 C) (mm) | 0.12 | 0.12 | 0.12 | 0.12 | 0.12 | 0.12 |
| d (20 C) (mm) | 1 | 1 | 1 | 1 | 1 | 1 |
| ΔP (psi) | 5 | 5 | 5 | 5 | 5 | 5 |
| L (20 C) (cm) | 8 | 8 | 8 | 8 | 8 | 8 |

| ΔT (° C.) | Ex. 16 Double layer | Ex. 17 Double layer | Ex. 18 Double layer | Ex. 19 Double layer | Ex. 20 Double layer | Ex. 21 Double layer |
|---|---|---|---|---|---|---|
| −15 | 0.9625 | 0.8533 | 0.8963 | 0.9525 | 0.823 | 0.9026 |
| −10 | 0.9942 | 0.9137 | 0.9456 | 0.9869 | 0.8911 | 0.9502 |
| −5 | 1.0061 | 0.9622 | 0.9797 | 1.0021 | 0.9498 | 0.9822 |
| 0 | 0.9984 | 0.9984 | 0.9984 | 0.9984 | 0.9984 | 0.9984 |
| 5 | 0.9721 | 1.0221 | 1.0019 | 0.9765 | 1.0367 | 0.999 |
| 10 | 0.9283 | 1.033 | 0.9903 | 0.9374 | 1.0642 | 0.9842 |
| 15 | 0.8684 | 1.0311 | 0.9641 | 0.8823 | 1.0805 | 0.9546 |
| 20 | 0.7947 | 1.017 | 0.9245 | 0.8134 | 1.0861 | 0.9116 |
| e | 0.00015 | 0.00015 | 0.00015 | 0.00015 | 0.00015 | 0.00015 |
| E | 0.000093 | 0.000093 | 0.000093 | 0.000093 | 0.000093 | 0.00008 |
| μ (20 C) (mPa · s) | 0.001 | 0.001 | 0.001 | 0.001 | 0.001 | 0.001 |
| C (20 C) (mm) | 0.12 | 0.12 | 0.11 | 0.1 | 0.13 | 0.12 |
| d (20 C) (mm) | 1.1 | 0.9 | 1 | 1 | 1 | 0.9 |
| ΔP (psi) | 5 | 5 | 5 | 5 | 5 | 5 |
| L (20 C) (cm) | 8 | 8 | 8 | 8 | 8 | 8 |

Figure 7:
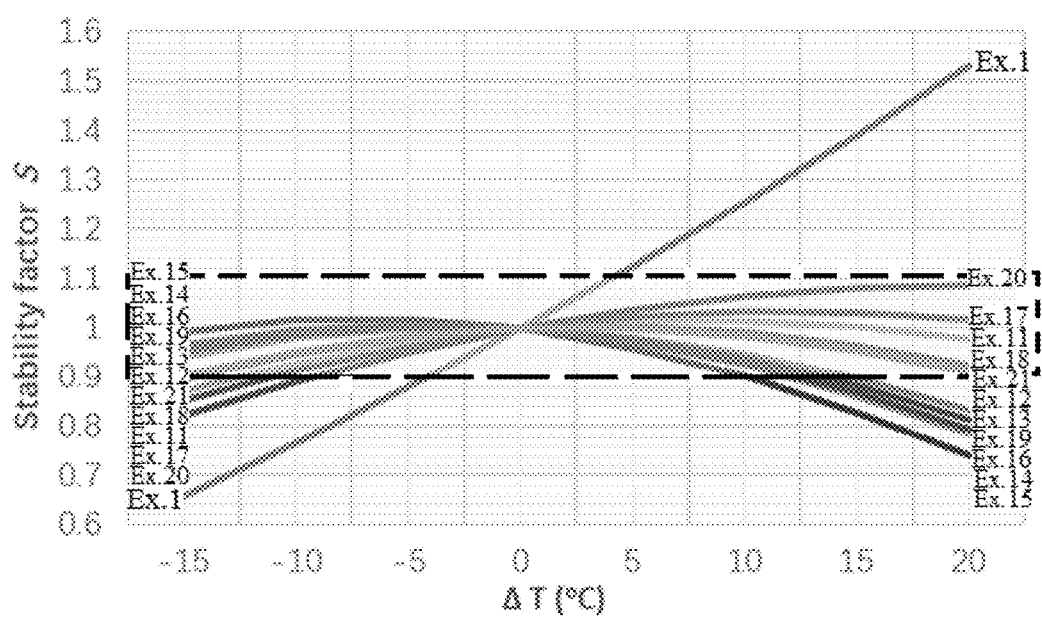
FIG. 7 is a curve chart of the stability factor S of the simulation result of several examples of the temperature compensation flow-limiting device adopting a double-layer structure in accordance with the present invention.

Based upon the data in Table 6, FIG. 7 has been drawn and shows the stability factors of various combinations among the parameters E, e, $C_o$, $d_o$ and ΔP at various temperature gaps. The stability factors S in the dotted area presents the flow volume of the capillary to be stable without under-infusion and over-infusion problems. If we look at the data in Ex. 1 (the single-layered capillary), it shows very poor flow volume stability and its S is mostly out of the safety zone. The S factors of examples 12 & 21 are all within the dotted area and are good examples of type 6 capillaries.

The double-layer capillary shows highly stable flow rate and the merit that the stability factor S is capable of self-justification when temperature changes from its initial state. It is proved that, as shown in Table 7 and FIG. 8, parameters of fluid viscosity (μ), S of single-layer capillary and double-layer capillary were selected for comparison at various temperature gap (ΔT) using a positive thermal expansion coefficient material. S of single-layer capillary shows linear relationship with liquid viscosity μ when temperature changes. On the contrary, the stability factor S of double-layer capillary can be made to be independent of viscosity μ changes whether the temperature goes up or down.

Figure 8:
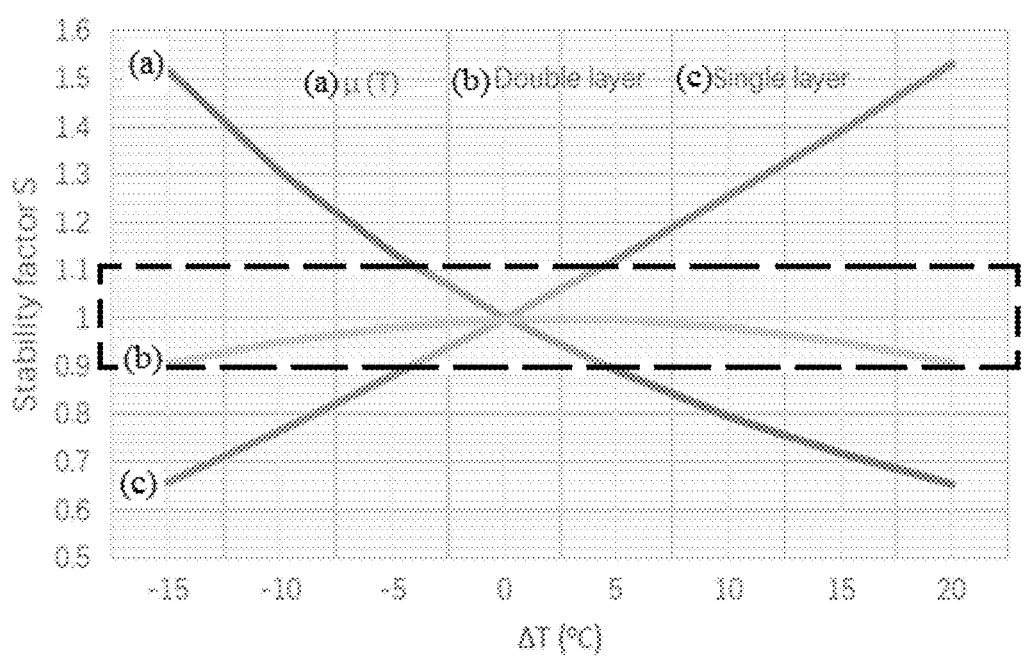
FIG. 8 is a curve comparison chart of the stability factor S of the simulation result of the temperature compensation flow-limiting device adopting a single-layer structure and double-layer structure, and the fluid viscosity (p) in different temperature gaps in accordance with the present invention.
Figure 9:
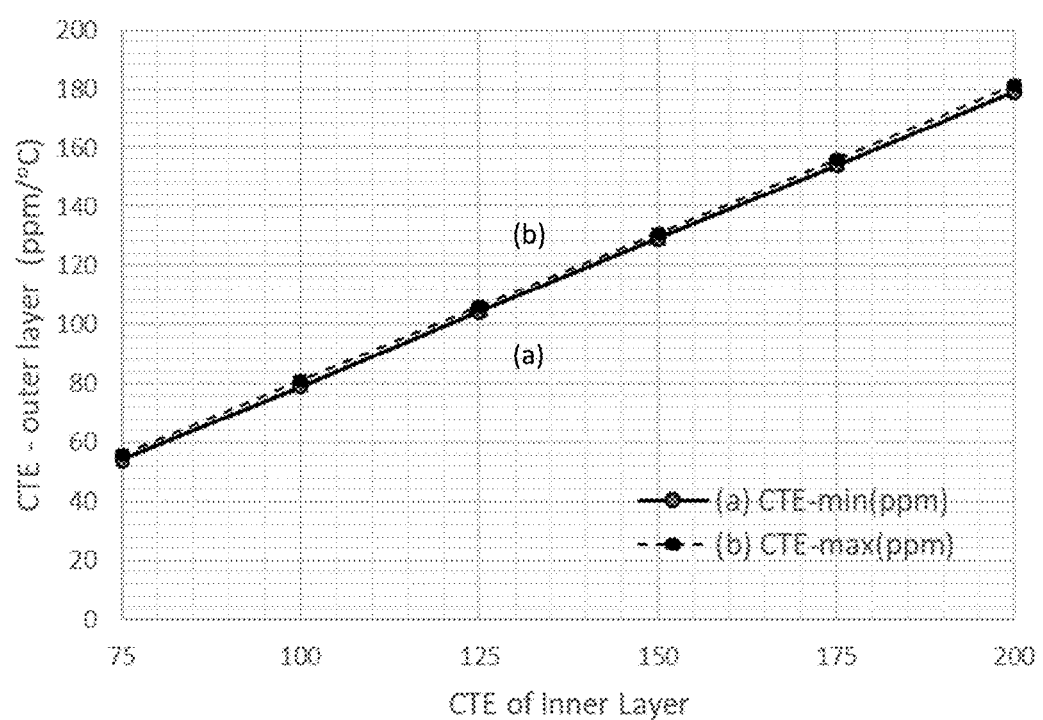
FIG. 9 is a curve chart of the CTE of the inner layer compared with the CTE of the outer layer of the temperature compensation flow-limiting device adopting a double-layer structure in accordance with the present invention.
Figure 10:
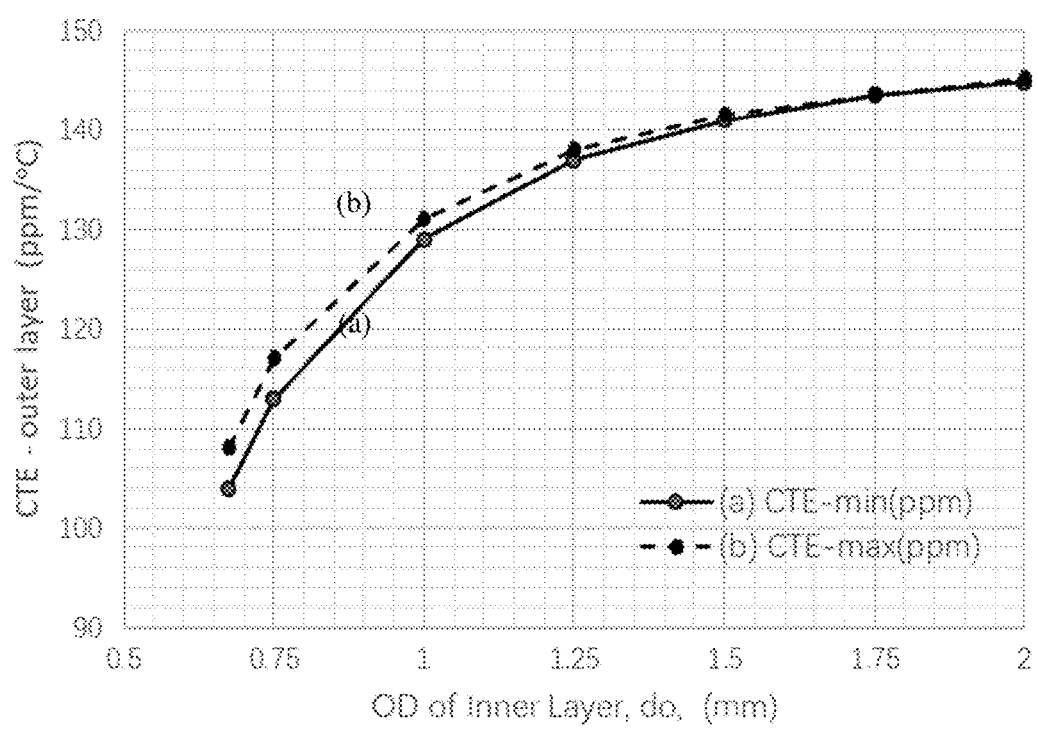
FIG. 10 is a curve chart of the CTE of the outer layer compared with the external diameter of the inner layer of the temperature compensation flow-limiting device adopting a double-layer structure in accordance with the present invention.

As shown in Table 7 and FIG. 8, the factor S of the double-layered capillaries (Ex. 12) shows good behavior of self-justification at different ΔT and always keep itself within the safety zone of 0.9 to 1.1. One of the reasons to explain this phenomenon is that the expansion of the soft inner layer is constrained by the rigid outer layer as temperature increases.

TABLE 7

| | | Stability Factor S | |
|---|---|---|---|
| ΔT (° C.) | Viscosity μ (T) | Single layer (Type I) Ex. 1 | Double layer (Type II) Ex. 12 |
| −15 | 1.5182 | 0.6587 | 0.9043 |
| −10 | 1.3059 | 0.7658 | 0.9515 |
| −5 | 1.1375 | 0.8791 | 0.9829 |
| 0 | 1.0016 | 0.9984 | 0.9984 |
| 5 | 0.89 | 1.1236 | 0.9982 |
| 10 | 0.7972 | 1.2544 | 0.9826 |
| 15 | 0.7192 | 1.3904 | 0.952 |
| 20 | 0.6527 | 1.5321 | 0.908 |

Thus, the expansion of the inner layer moves towards the core portion and reduces the diameter of core; i.e., C(T) becomes less than $C_o$. Thus, as temperature goes up, the stability of volumetric flow rate is achieved when the increase of flow rate due to decrease in viscosity μ is compensated by the expansion of core diameter C(T). As the temperatures decrease, an opposite process may take place to compensate the higher viscosity by the contraction of the inner layer outward, which increase the diameter of the inner lumen. For a conventional single-layered capillary shown in FIG. 6 (Ex. 1), the diameter of core is mainly affected by the ambient temperature, following the rule of hot/expand and cold/contract for a positive thermal expansion coefficient material. Under such circumstance, deviation of the flow rate is linearly proportional to ΔT as shown in FIG. 6 and it becomes easily out of the safety range. The simulated results successfully prove that a capillary of double-layered core-shell structure, of which it consisting of a soft inner layer and a rigid outer layer, is an appropriate method to solve the problem of flow-stability in the capillary defined as above.

The above simulation result shows that it is not only able to achieve a high negative thermal expansion effect by the characteristics originally owned by the material, such as using the material with a high negative CTE to serve as a single-layer capillary tube, but is also able to achieve the above effect by the structure design according to the present invention. The double-layer capillary tube consisting of a soft inner layer and a hard outer layer can make the outer layer limit the thermal expansion of the inner layer so as to generate a high negative thermal expansion effect of the size of the inner channel of the capillary tube and then further resist influence, caused by the temperature, to the viscosity of the fluid, which is a proper invention capable of solving the flow stability problem of the currently available capillary tubes. The outer layer can have any structure, thickness or flex modulus; the outer layer can just conform to the requirements of the present invention if the outer layer can constraint or limit the inner layer to achieve the aforementioned effect.

Figure 11:
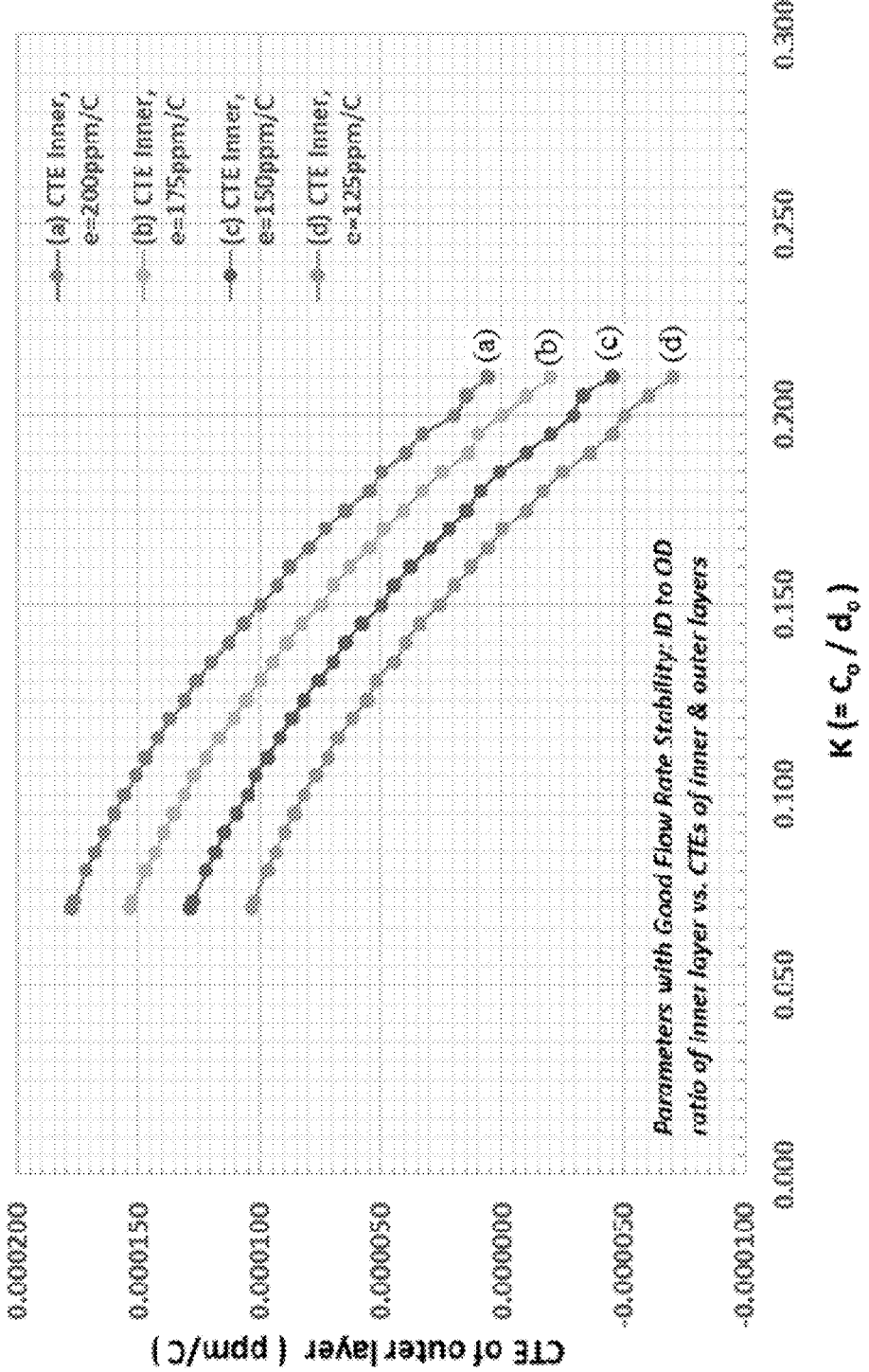
FIG. 11 is a curve chart of the CTE of the outer layer compared with the ratio of the internal diameter to the external diameter of the inner layer of the temperature compensation flow-limiting device adopting a double-layer structure in accordance with the present invention.

Further, the selection regulations of the aforementioned materials of temperature compensation flow-limiting structure 10 with a double-layer structure are as follows:

Furthermore, according to FIG. 11, when the difference between the CTE of the inner layer and the CTE of the outer layer is large enough, the ratio (k) of the diameter of the inner channel of the inner layer to the outer diameter of the inner layer is greater than 0 but less than 0.3; the preferred range of the ratio (k) is greater than 0 but less than 0.24.

Figures 12A, 12B:
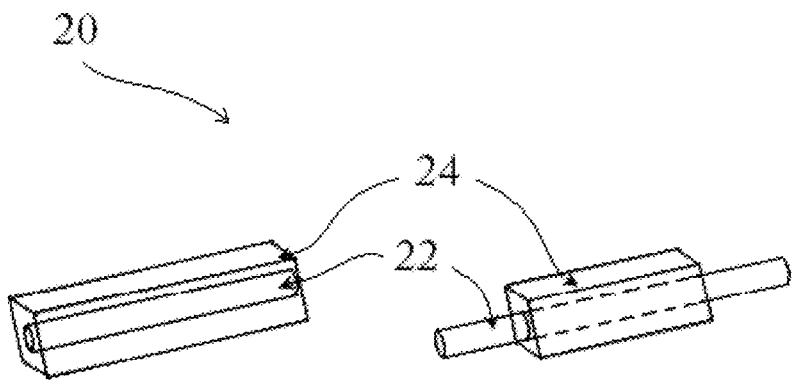
FIG. 12(a) and FIG. 12(b) are schematic views of the inner layer aligned with the outer layer and the inner layer not aligned with the outer layer of another temperature compensation flow-limiting device in accordance with the present invention.

Additionally, inner layer 12 and outer layer 14, in temperature compensation flow-limiting device 10, can not only be manufactured by the aforementioned co-extrusion or injection molding, but can also be manufactured by pouring technique to surround the outer surface of the inner layer by pouring a stiff outer layer material (e.g., cement). As temperature compensation flow-limiting device 20 shown in FIG. 12, the two ends of inner layer 22 are aligned with the two ends of outer layer 24, as shown in FIG. 12(*a*), or the two ends of inner layer 22 protrude from the two ends of outer layer 24 as shown in FIG. 12(*b*).

Figure 13:
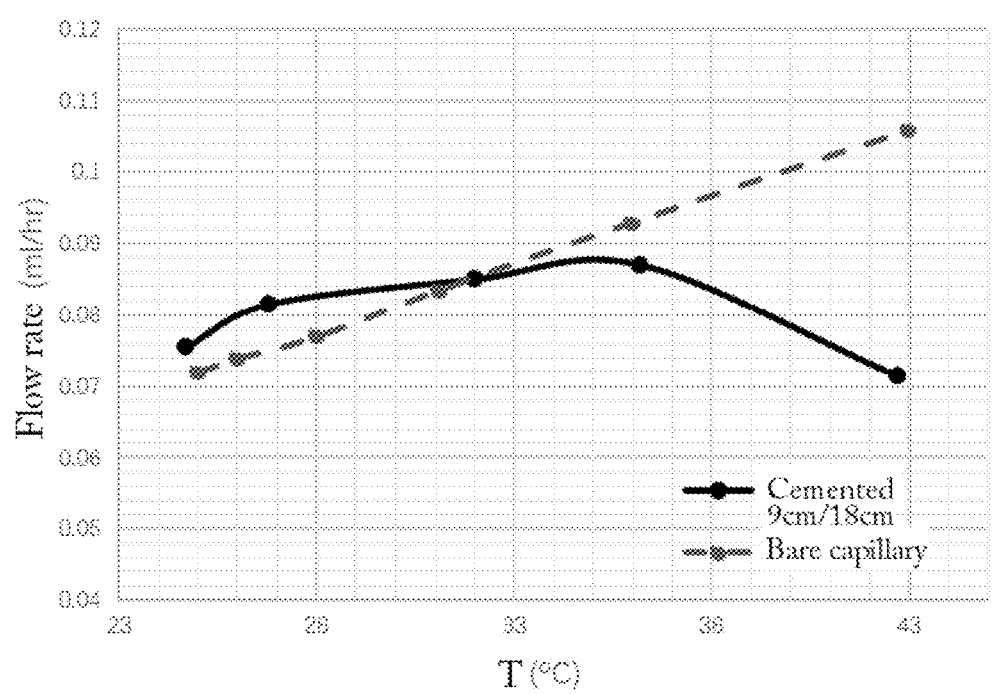
FIG. 13 is a curve chart of the flow velocity compared with the temperature of the temperature compensation flow-limiting device and the elastomeric infusion system in accordance with the present invention.
Figure 14:
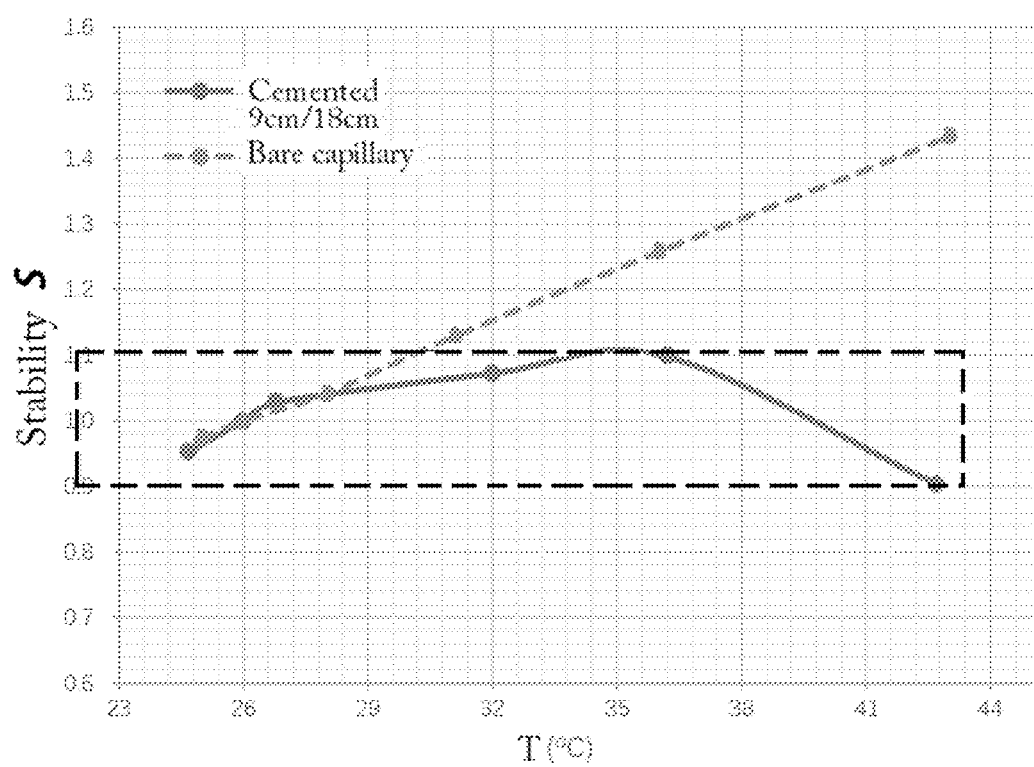
FIG. 14 is a curve chart of the stability factor compared with the temperature of the temperature compensation flow-limiting device and the elastomeric infusion system in accordance with the present invention.

The temperature compensation fluid-limiting device 20 was used for the test. The length of the capillary is 18 cm and diameter of core (hollow conduit) is measured to be 0.2 mm and outside diameter to be 2.5 mm. The pressure of the infuser bladder is 4 psi. Volumetric flow rate is 4 ml/hr. described in the product brochure. In FIG. 13, it shows the flow rate is a function of temperature. The dashed-line follows a linear relationship between the flow rate of the infusion system and temperature. When part of the capillary was embedded by a polymeric cement with both ends opened, the flow rate changes its behavior as temperature varies, as shown by the solid-line curve. The CTE of the potting polymeric material, in which cement has been selected as the filler, is ca. 85 ppm/° C. and the embedded section is around 50% of the total capillary length. As shown in FIG. 14, the curve of 50% cement-embedded sample shows good compatibility to those curves predicted by the mathematical model. The shape of the curve is concave downward that is similar to the simulated examples 12 and 21. The stability factor S of the 50% cement-encysted sample is all within the safety zone from temperatures 25° C. to 43° C. This example fully proves the approach that the flow rate of the capillary in an elastomeric infusion system can be stabilized and the temperature/viscosity effect can be minimized by using the double-layered core-shell structure with a rigid outer layer, which may fully or partially encapsulate the inner layer.

While the means of specific embodiments in the present invention have been described by reference drawings, numerous modifications and variations could be made thereto by those skilled in the art without departing from the scope and spirit of the invention set forth in the claims. The modifications and variations should being a range limited by the specification of the present invention.

What is claimed is:

1. A temperature compensation flow-limiting device, configured to be disposed in disposed in an infusion tube of an infusion system to improve instability, caused by temperature change, of the flow velocity of a medicinal solution inside the infusion tube and comprising at least one inner layer and at least one outer layer bonded to an outer side of the inner layer to avoid the inner layer being separated from the outer layer when in use, wherein the coefficient of thermal expansion (CTE) of the inner layer is greater than the coefficient of thermal expansion of the outer layer, and make the flow rate stability coefficient S in the following range: 1.1>S>0.9, $$S = \frac{Q(T)}{Q_o} = \left(\frac{C(T)}{C_o}\right)^4 \cdot \left(\frac{1}{1+E\cdot\Delta T}\right) \cdot \left(\frac{1}{1.022\ e^{-0.024-\Delta T}}\right),$$

where Q(T) is the flow rate of the inner layer when the temperature is T, Qo is the flow rate of the inner layer at the initial temperature, C(T) is the inner cavity diameter of the inner layer when the temperature is T, Co is the inner cavity diameter of the inner layer at the initial temperature, E is the thermal expansion coefficient of the outer layer, e is the thermal expansion coefficient of the inner layer, $\Delta T$ is the temperature difference, the inner layer expands when the temperature of the fluid inside the infusion path increases, the internal diameter of the inner layer decreases as it is limited by the outer layer, the inner layer shrinks when the temperature of the fluid inside the infusion tube decreases, and the internal diameter of the inner layer increases as it is limited by the outer layer.

2. The temperature compensation flow-limiting device of claim 1, wherein the inner layer is tubular and has an inner channel, and the inner channel is tubular and is used for transporting fluid.

3. The temperature compensation flow-limiting device of claim 2, wherein the diameter of the inner channel of the inner layer is Co and the outer diameter of the inner layer is do, when a cross-section of the inner layer or the inner channel is not circular, equivalent diameters of the inner layer are Co and do, and the equivalent diameters of the inner layer are calculated according to the area of the cross-section.

4. The temperature compensation flow-limiting device of claim 3, wherein the inner channel of the inner layer is either eccentric or concentric.

5. The temperature compensation flow-limiting device of claim 3, wherein if the thermal expansion coefficient difference between the inner layer and the outer layer is large enough, the ratio k (k=Co/do) of the diameter (Co) of the inner channel of the inner layer to the outer diameter (do) of the inner layer is greater than 0.

6. The temperature compensation flow-limiting device of claim 5, wherein the ratio (k) of the diameter of the inner channel of the inner layer to the outer diameter of the inner layer is less than 0.3.

7. The temperature compensation flow-limiting device of claim 6, wherein the ratio k of the inner layer is greater than 0 but less than 0.24.

8. The temperature compensation flow-limiting device of claim 2, wherein the inner side of the inner layer and the outer side of the outer layer further comprise several supplementary layers to provide additional medical-care functions.

9. The temperature compensation flow-limiting device of claim 1, wherein the inner layer and the outer layer are made of different materials.

10. The temperature compensation flow-limiting device of claim 1, wherein the inner layer and the outer layer are made of the same material, but the outer layer further comprises materials with negative thermal expansion (NTE) and/or low coefficient of thermal expansion (CTE).

11. The temperature compensation flow-limiting device of claim 1, wherein the inner layer and the outer layer are made of the same material, but the inner layer and the outer layer are different in composition or ratio, or comprise different plasticizers, stabilizers or other additives, whereby the inner layer and the outer layer have different coefficients of thermal expansion.

12. The temperature compensation flow-limiting device of claim 1, wherein the inner layer and the outer layer are made of the same material or different materials, and the materials of the inner layer and the outer layer are either polymer, ceramic, glass or metal.

13. The temperature compensation flow-limiting device of claim 1, wherein the inner side of the inner layer and the outer side of the outer layer further comprise several supplementary layers to provide additional medical-care functions.

\* \* \* \* \*